United States Patent
Darois et al.

(12) 
(10) Patent No.: US 6,258,124 B1
(45) Date of Patent: Jul. 10, 2001

(54) PROSTHETIC REPAIR FABRIC

(75) Inventors: Roger E. Darois, Foster; Stephen N. Eldridge, Exeter; Dennis Cherok, North Smithfield; Ronald L. Greene, Warwick, all of RI (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/309,071

(22) Filed: May 10, 1999

(51) Int. Cl.[7] ............................................. A61F 2/08
(52) U.S. Cl. ............................. 623/14.13; 623/11.11; 606/151
(58) Field of Search ................... 623/11.11, 14.13; 606/151

(56) References Cited

U.S. PATENT DOCUMENTS

| | | |
|---|---|---|
| 2,621,145 | 12/1952 | Sano . |
| 2,671,444 | 3/1954 | Pease, Jr. . |
| 3,054,406 | 9/1962 | Usher . |
| 3,272,204 | 9/1966 | Artandi et al. . |
| 3,625,209 | 12/1971 | Clark . |
| 4,051,848 | 10/1977 | Levine . |
| 4,400,833 | 8/1983 | Kurland . |
| 4,576,608 | 3/1986 | Homsy . |
| 4,585,458 | 4/1986 | Kurland . |
| 4,633,873 | 1/1987 | Dumican et al. . |

(List continued on next page.)

FOREIGN PATENT DOCUMENTS

| | | |
|---|---|---|
| 2114282 | 7/1994 | (CA) . |
| 298 17 682 U1 | 4/1999 | (DE) . |
| 0 194 192 A1 | 9/1986 | (EP) . |
| 0 334 046 A2 | 2/1989 | (EP) . |
| 0 358 819 A1 | 3/1990 | (EP) . |
| 0 719 527 A1 | 7/1996 | (EP) . |

(List continued on next page.)

OTHER PUBLICATIONS

Gregory L. Brown, M.D. et al., "Comparison of Prosthetic Materials for Abdominal Wall Reconstruction in the Presence of Contamination and infections", Annals Of Surgery, Jun. 1985, vol. 201, pp. 705–711.

Scott D. Jenkins, M.D. et al., A Comparison of Prosthetic Materials Used to Repair Abdominal Wall Defects;, Surgery, Aug. 1983, vol. 94, No. 2, pp. 392–398.

(List continued on next page.)

Primary Examiner—Jeffrey A. Smith
(74) Attorney, Agent, or Firm—Wolf, Greenfield & Sacks, P.C.

(57) ABSTRACT

A prosthetic repair fabric and method for repairing an inguinal hernia in the inguinal canal. The prosthesis including a layer of mesh fabric that is susceptible to the formations of adhesions with sensitive tissue and organs, and a barrier layer that inhibits the formation of adhesions with sensitive tissue and organs. The mesh fabric including a medial section and a lateral section that are configured to be positioned adjacent the medial corner and the lateral end of the inguinal canal, respectively, when the prosthesis is placed in the inguinal canal to repair the defect. The barrier layer is positioned on the mesh fabric to inhibit the formation of adhesions between the spermatic cord and the mesh fabric. At least a portion of the lateral section of the mesh fabric is free of the barrier layer on both of its sides to promote enhanced tissue ingrowth therein. The barrier layer may include at least one flap that is to be folded through the mesh fabric to isolate the spermatic cord from internal edges of the fabric when the spermatic cord is routed through the prothesis.

40 Claims, 9 Drawing Sheets

U.S. PATENT DOCUMENTS

| | | |
|---|---|---|
| 4,655,221 | 4/1987 | Devereux . |
| 4,693,720 | 9/1987 | Scharnberg et al. . |
| 4,725,279 | 2/1988 | Woodroof . |
| 4,769,038 | 9/1988 | BendaVID ET AL. . |
| 4,854,316 | 8/1989 | Davis . |
| 4,882,162 | 11/1989 | Ikada et al. . |
| 4,942,875 | 7/1990 | Hlavacek et al. . |
| 4,997,440 | 3/1991 | Dumican . |
| 5,002,551 | 3/1991 | Linsky et al. . |
| 5,007,916 | 4/1991 | Linsky et al. . |
| 5,092,884 | 3/1992 | Devereux et al. . |
| 5,100,422 | 3/1992 | Berguer et al. . |
| 5,104,400 | 4/1992 | Berguer et al. . |
| 5,116,357 | 5/1992 | Eberbach . |
| 5,116,360 | 5/1992 | Pinchuk et al. . |
| 5,122,155 | 6/1992 | Eberbach . |
| 5,141,515 | 8/1992 | Eberbach . |
| 5,141,522 | 8/1992 | Landi . |
| 5,147,401 | 9/1992 | Bakker et al. . |
| 5,222,987 | 6/1993 | Jones . |
| 5,254,133 | 10/1993 | Seid . |
| 5,258,000 | 11/1993 | Gianturco . |
| 5,290,217 | 3/1994 | Campos . |
| 5,326,355 | 7/1994 | Landi . |
| 5,334,217 | 8/1994 | Das . |
| 5,356,432 | 10/1994 | Rutkow et al. . |
| 5,366,460 | 11/1994 | Eberbach . |
| 5,368,602 | 11/1994 | de la Torre . |
| 5,370,650 | 12/1994 | Tovey et al. . |
| 5,425,740 | 6/1995 | Hutchinson, Jr. . |
| 5,433,996 | 7/1995 | Kranzler et al. . |
| 5,456,720 | 10/1995 | Schultz et al. . |
| 5,461,885 | 10/1995 | Yokoyama et al. . |
| 5,480,436 | 1/1996 | Bakker et al. . |
| 5,508,036 | 4/1996 | Bakker et al. . |
| 5,519,004 | 5/1996 | Urry . |
| 5,545,178 * | 8/1996 | Kensey et al. .................. 606/213 |
| 5,569,273 | 10/1996 | Titone . |
| 5,593,441 | 1/1997 | Lichtenstein et al. . |
| 5,601,579 | 2/1997 | Semertzides . |
| 5,614,284 | 3/1997 | Kranzler et al. . |
| 5,634,931 | 6/1997 | Kugel . |
| 5,695,525 | 12/1997 | Mulhauser et al. . |
| 5,697,978 | 12/1997 | Sgro . |
| 5,716,408 | 2/1998 | Eldridge et al. . |
| 5,716,409 | 2/1998 | Debbas . |
| 5,722,992 | 3/1998 | Goldman . |
| 5,725,577 | 3/1998 | Saxon . |
| 5,733,337 | 3/1998 | Carr, Jr. et al. . |
| 5,743,917 | 4/1998 | Saxon . |
| 5,766,246 | 6/1998 | Mulhauser et al. . |
| 5,769,864 | 6/1998 | Kugel . |
| 5,813,975 | 9/1998 | Valenti . |
| 5,916,225 | 6/1999 | Kugel . |
| 6,004,333 * | 12/1999 | Sheffield et al. .................. 606/151 |
| 6,066,776 * | 5/2000 | Goodwin et al. ............... 606/151 X |
| 6,120,539 * | 9/2000 | Eldridge et al. ................. 623/11.11 |
| 6,174,320 * | 1/2001 | Kugel et al. ....................... 606/151 |
| 6,176,863 * | 1/2001 | Kugel et al. ....................... 606/151 |

FOREIGN PATENT DOCUMENTS

| | | |
|---|---|---|
| 0 560 934 | 8/1996 | (EP) . |
| 0 827 742 A2 | 3/1998 | (EP) . |
| 0 362 113 | 4/1999 | (EP) . |
| 2 744 906 A1 | 8/1997 | (FR) . |
| 1 352 282 | 6/1972 | (GB) . |
| 1 406 271 | 9/1975 | (GB) . |
| 1718857 | 3/1992 | (SU) . |
| WO 82/04390 | 12/1982 | (WO) . |
| WO 90/14796 | 12/1990 | (WO) . |
| WO 92/10218 | 6/1992 | (WO) . |
| WO 92/19162 | 11/1992 | (WO) . |
| WO 93/17635 | 9/1993 | (WO) . |
| WO 94/17747 | 8/1994 | (WO) . |
| WO 96/09795 | 4/1996 | (WO) . |
| WO 96/14805 | 5/1996 | (WO) . |
| WO 97/35533 | 10/1997 | (WO) . |
| WO 98/14134 | 4/1998 | (WO) . |
| WO 00/07520 | 2/2000 | (WO) . |

OTHER PUBLICATIONS

Hernando Cordona, M.D., "Prosthokeratoplasty", 1983, Cornea, vol. 2, No. 3, 1983, pp. 179–183.

Interceed(TC7) Adhesion Barrier Study Group (Cohen, Stephen M., et al.), Prevention of postsurgical adhesions by Interceed(TC7), *an absorbable adhesion barrier: a prospective, randomized multicenter clinical study, Fertility and Sterility, vol. 51, No. 6, Jun. 1989.

Alonzo P. Walker, M.D., James Henderson, D.V.M. and Robert E. Condon, M.D., "Double–Layer Prostheses for Repair of Abdominal Wall Defects in a Rabbit Model.", Jun. 1992.

Robert G. Uzzo et al., "The Effects of Mesh Bioprosthesis on the Spermatic Cord Structures: A Preliminary Report in a Canine Model", The Journal Of Urology, Apr. 1999, vol. 161, pp. 1344–1349.

* cited by examiner

PROSTHETIC REPAIR FABRIC

FIELD OF THE INVENTION

The present invention relates to a prosthetic repair fabric and, more particularly, to an adhesion resistant fabric for use in soft tissue repair and reconstruction.

DISCUSSION OF RELATED ART

Various prosthetic mesh materials have been proposed to reinforce the abdominal wall and to close abdominal wall defects. In certain procedures, the prosthetic mesh may come into contact with sensitive tissue or organs potentially leading to postoperative adhesions between the mesh and the sensitive tissue or organs. There has been a suggestion that, in an inguinal hernia repair, the prosthetic mesh may come into direct contact with the spermatic cord. Postoperative adhesions between the mesh and the spermatic cord and/or erosion of the mesh into the cord, were they to occur, could potentially affect spermatic cord structure and function.

Inguinal hernias are commonly repaired using a sheet of mesh fabric, such as BARD MESH, which may be trimmed, as necessary, to match the particular size and shape of the inguinal floor. A slit is preformed or made by the surgeon from the lateral end of the mesh opposite the medial corner of the inguinal canal toward the medial end of the mesh to form a pair of lateral tails that are separated to receive the spermatic cord therebetween. The tails may then be overlapped to encircle the cord and reinforce the internal ring. A preshaped mesh may be provided with the slit and a keyhole at the end of the slit for receiving the cord therein.

Uzzo et al., "The Effects of Mesh Bioprosthesis on the Spermatic Cord Structures: A Preliminary Report in a Canine Model", The Journal of Urology, Vol. 161, April 1999, pp. 1344–1349, reports that prosthetic mesh in direct contact with the spermatic cord may adversely affect spermatic cord structure and function. The article suggests that the interposition of autologous fat between the mesh and the cord during open inguinal repair may prove beneficial.

Various approaches to reducing the incidence of postoperative adhesions arising from the use of prosthetic mesh materials have been proposed by the prior art. It had been proposed in U.S. Pat. No. 5,593,441, assigned to C. R. Bard, Inc., also the assignee of the present application, to repair ventral hernias and/or reconstruct chest walls using a prosthesis that is covered with an adhesion resistant barrier, such as a sheet of expanded PTFE. In the repair of ventral hernias and in chest wall reconstruction, the composite is positioned with the barrier relative to the region of potential adhesion, such as the abdominal viscera.

International Publication No. WO 97/35533 proposed a universal composite prosthesis in which one side of a layer of mesh material is completely covered with a layer of barrier material. The mesh material promotes biological tissue ingrowth while the barrier material retards biological tissue adherence thereto. The prosthesis may be utilized for various surgical procedures, including ventral hernia repair and inguinal hernia repair in which the barrier material is positioned adjacent the sensitive tissue. For an inguinal hernia, the barrier material is positioned adjacent the spermatic cord to retard adhesions thereto and the mesh material is positioned adjacent muscle tissue to promote tissue adhesion thereto.

It is an object of the present invention to provide an improved method and prosthesis for the repair of inguinal hernias.

SUMMARY OF THE INVENTION

The present invention is a composite prosthetic repair fabric and method for reinforcing and repairing a tissue or wall defect by promoting enhanced tissue ingrowth thereto, while limiting the incidence of postoperative adhesions between the mesh and sensitive tissue or organs. The composite is formed of a biologically compatible, flexible implantable fabric suitable for reinforcing tissue and closing tissue defects, and a barrier for physically isolating the reinforcing fabric from areas likely to form adhesions. The barrier and implantable fabric may be attached by stitching, an adhesive, fusion or insert molding in a manner which preserves sufficient openings in the fabric for tissue ingrowth.

The prosthetic repair fabric is particularly suited for repairing a tissue or muscle wall defect located in the inguinal canal near the spermatic cord, the inguinal canal having a medial corner and a lateral end. The prosthetic repair fabric comprises a layer of mesh fabric with a plurality of interstices that are constructed and arranged to allow tissue ingrowth, the mesh fabric being susceptible to the formation of adhesions with sensitive tissue and organs. The mesh fabric includes a medial section and a lateral section that are configured to be positioned adjacent the medial corner and the lateral end of the inguinal canal, respectively, when the prosthetic repair fabric is placed in the inguinal canal. The prosthetic repair fabric further comprises at least one barrier layer that inhibits the formation of adhesions with sensitive tissue and organs, the barrier layer being disposed on at least one side of the layer of mesh fabric to inhibit the formation of adhesions between the spermatic cord and the mesh fabric.

In one embodiment of the invention, the barrier layer covers at least a portion of the medial section that is to be positioned adjacent the spermatic cord when the prosthetic repair fabric is placed in the inguinal canal. At least a portion of the lateral section of the mesh fabric is free of the barrier layer on both sides thereof to promote enhanced tissue ingrowth therein.

In another embodiment of the invention, the barrier layer includes at least one flap constructed and arranged to be folded through the mesh fabric to isolate the spermatic cord from internal edges of the mesh fabric when the spermatic cord is routed through the prosthesis.

Other objects and features of the present invention will become apparent from the following detailed description when taken in connection with the accompanying drawings. It is to be understood that the drawings are designed for the purpose of illustration only and are not intended as a definition of the limits of the invention.

BRIEF DESCRIPTION OF THE DRAWINGS

The foregoing and other objects and advantages of the invention will be appreciated more fully from the following drawings, wherein like reference characters designate like features, in which.

DESCRIPTION OF ILLUSTRATIVE EMBODIMENTS

Figure 1:
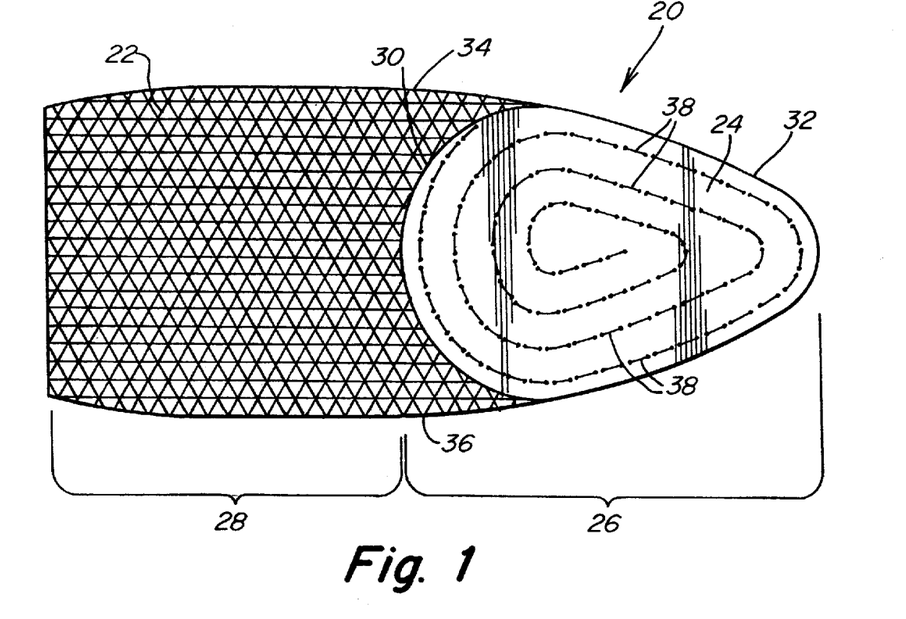
FIG. 1 is a top plan view of a prosthetic repair fabric in accordance with one illustrative embodiment of the present invention.
Figure 2:
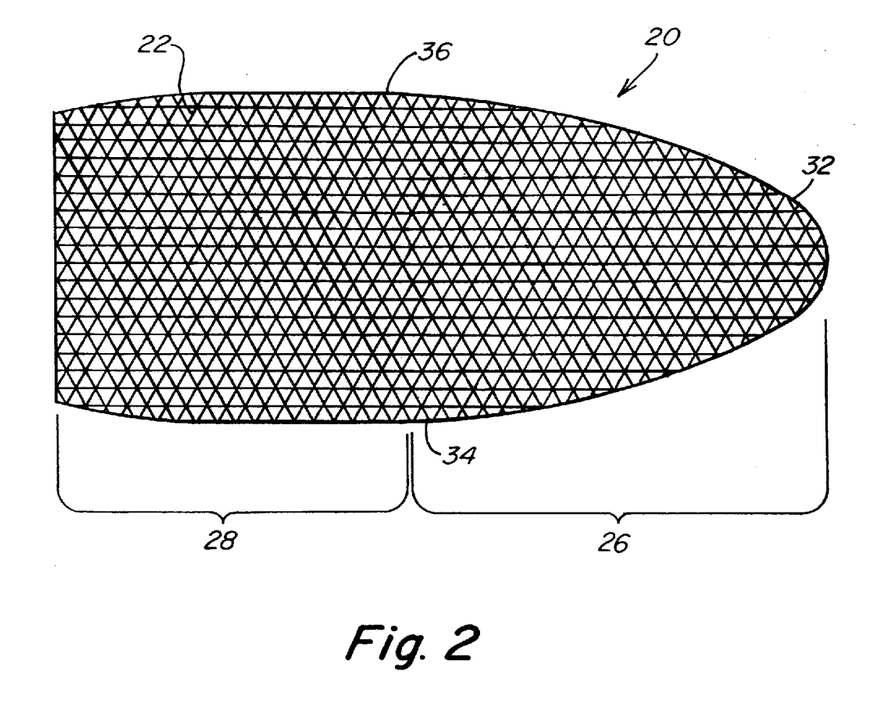
FIG. 2 is a bottom plan view of the prosthetic repair fabric of FIG. 1.

FIGS. 1–2 illustrate one embodiment of a composite prosthetic repair fabric for repairing soft tissue and wall defects, particularly inguinal hernias, by promoting enhanced tissue ingrowth while limiting the incidence of postoperative adhesions to the repair fabric. The prosthesis 20 includes a tissue infiltratable fabric 22 and an adhesion resistant barrier 24. The fabric 22 is formed of a biologically compatible, flexible material that includes a plurality of interstices or openings which allow sufficient tissue ingrowth to secure the composite to host tissue after implantation. The barrier 24 is formed of a material that does not substantially stimulate tissue ingrowth and adhesion formation when implanted in tissue to limit the incidence of postoperative tissue adhesions between the fabric and adjacent sensitive tissue and organs. A portion of the prosthesis remains completely free of barrier material on both sides of the fabric to enhance tissue ingrowth thereto.

The composite prosthesis 20 is relatively flat and sufficiently pliable to allow a surgeon to manipulate the shape of the implant to conform to the anatomical site of interest and to be sutured or stapled thereto. The shape and size of the composite implant, and of the respective fabric 22 and barrier 24, may vary according to the surgical application as would be apparent to one of skill in the art. In this regard, it is contemplated that the fabric and/or barrier may be preshaped or shaped by the surgeon during the surgical procedure. The prosthesis may be provided with the barrier preattached to the fabric. Alternatively, the prosthesis may be provided as a kit of separate parts with the barrier either being attached to the fabric during the surgical procedure or simply overlaid on a desired portion of the fabric to be held in place by adjacent tissue and/or organs. It is also contemplated that two or more layers of fabric and/or barrier material may be implemented in the prosthesis.

The prosthesis 20 is particularly suited to the repair of inguinal hernias, in which the barrier 24 isolates the spermatic cord from the fabric 22, reducing the incidence of cord trauma associated with adhesion, erosion, constriction and the like which may result from an inflammatory reaction between the cord and the fabric. In the illustrative embodiment shown in FIGS. 1–2, the prosthesis 20 includes a medial section 26 and a lateral section 28 that are configured to be positioned adjacent the medial corner and the lateral end of the inguinal canal, respectively. The barrier 24 covers a substantial portion of one side of the medial section 26 and includes a lateral edge 30 that extends slightly beyond the center of the prosthesis toward the lateral section 28 so that the lateral edge 30 of the barrier is positioned adjacent the spermatic cord where it passes through the prosthesis. As illustrated, at least a portion, if not all, of the lateral section 28 of the prosthesis is completely free of the barrier material to expose both sides of the fabric in the lateral section and enhance tissue ingrowth thereto.

The medial section 26 of the prosthesis includes a generally rounded medial edge 32 that approximates the shape of the medial corner of the inguinal canal. The barrier 24 is generally configured with a thumb nail or tear drop shape that includes a rounded lateral edge 30 opposite the medial edge 32 of the prosthesis. This configuration maximizes the coverage of the barrier along the longitudinal axis of the prosthesis along which the spermatic cord will generally lie, while increasing the amount of exposed fabric along the side edges 34, 36 along the medial section of the prosthesis. As shown in FIG. 1, the width of the barrier 24 initially increases in a direction from the lateral edge 30 of the barrier toward the medial edge 32 of the prosthesis to ensure that a spermatic cord angled from the longitudinal axis of the prosthesis remains isolated from the mesh fabric.

The fabric 22 and barrier 24 may be configured to have any suitable shape that maximizes both cord isolation from the mesh and tissue ingrowth with the mesh. Examples of other barrier shapes include, but are not limited to, parabolic, semi-elliptical and rectangular shapes.

The tissue infiltratable fabric 22 includes a plurality of interstices or pores which are of sufficient size and orientation to allow tissue ingrowth. The barrier 24 is connected to the fabric 22 without detrimentally limiting the tissue infiltration.

In the illustrative embodiment, the fabric 22 and the barrier 24 are integrally connected with a continuous series of connecting stitches 38. As shown in FIG. 1, the stitches 38 may be formed in a concentric spiral pattern that follows the shape of the barrier 24 to provide a high density of attachment points between the barrier 24 and fabric 22. Stitching may be beneficial to allow total tissue infiltration to the fabric. The concentric spiral pattern also maintains composite integrity by preventing the barrier 24 and underlying fabric 22 from separating when the medial section 26 of the prosthesis is trimmed by the surgeon to match a particular size and shape of the medial corner of the inguinal canal.

Figure 3A:
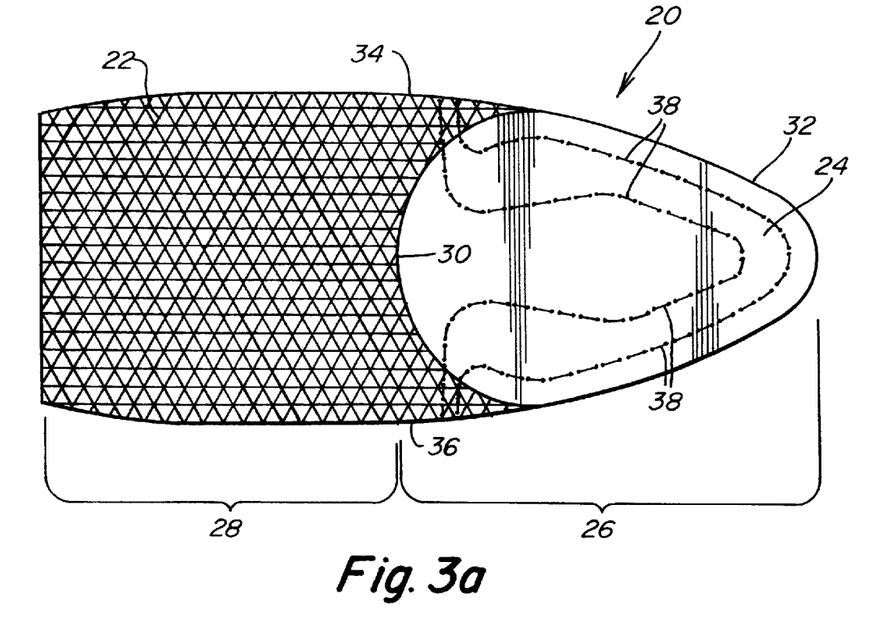
FIGS. 3a and 3b are top plan views of a prosthetic repair fabric illustrating several other embodiments of a stitch pattern for attaching the barrier to the fabric.
Figure 3B:
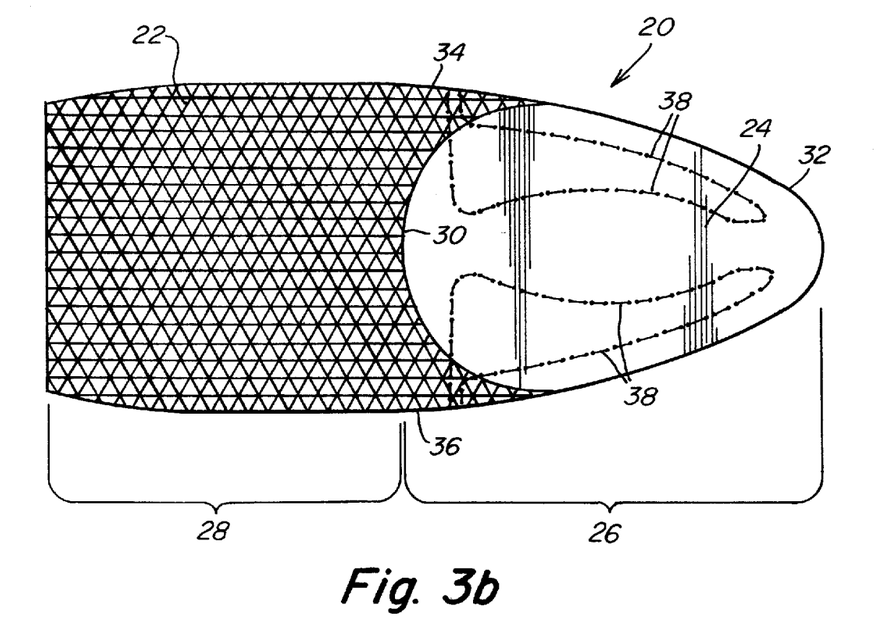

In other illustrative embodiments as shown in FIGS. 3a–3b, the stitch pattern may include a pair of continuous stitches 38 that begin and end on opposite side edges 34, 36 (FIG. 3a) or the same sides 34, 36 (FIG. 3b) of the prosthesis adjacent the lateral edge 30 of the barrier and generally follow the contour of the medial edge 32 of the prosthesis. These patterns maintain the central portion of the barrier adjacent the longitudinal axis of the prosthesis, along which the spermatic cord may generally lie, relatively free of stitches. It is to be appreciated, however, that any suitable type of stitch, such as an intermittent stitch, in any suitable stitch pattern, such as a serpentine pattern, may be employed to maintain the integrity of the composite while reducing the incidence of adhesions between the cord and the stitches.

In one embodiment, the stitches 38 are formed with a monofilament polypropylene yarn. The barrier 24 is positioned on the fabric 22 to face the sewing needle so that the locking portion of each stitch is formed on the fabric side of the composite rather than on the barrier side to reduce the incidence of localized adhesions with the spermatic cord. The stitches 38 may be formed using a #10 ball-tipped needle to reduce the potential incidence of tissue ingrowth through the stitch holes. The sheets of mesh and barrier material may be held by a frame during the sewing procedure on a computer controlled table that has been programmed with the desired stitch pattern.

Any other suitable fastening technique and material may be employed to attach the barrier 24 to the fabric 22. For example, the barrier 24 may be bonded to the fabric 22 using an adhesive dispensed in a desired pattern, such as a spiral pattern, a serpentine pattern or a grid-like pattern of dots or beads, that maintains a sufficient quantity of open or non-impregnated interstices for tissue infiltration. Alternatively, the barrier 24 may be laminated or heat fused to the fabric 22 by a combination of heat and pressure. This lamination technique may require the addition of a second layer of fabric to ensure sufficient tissue ingrowth. An example of a laminated prosthesis is described in pending U.S. patent application Ser. No. 08/850,217 which is also assigned to C. R. Bard, Inc., the assignee of the present application, and is incorporated herein by reference. The barrier may also be insert molded to the fabric using any suitable molding process.

In one embodiment, the fabric 22 is formed of a sheet of knitted polypropylene monofilament mesh fabric such as BARD MESH available from C. R. Bard, Inc. When implanted, the polypropylene mesh promotes rapid tissue ingrowth into and around the mesh structure. Alternatively, other surgical materials which are suitable for tissue reinforcement and defect closure may be utilized including PROLENE, SOFT TISSUE PATCH (microporous ePTEE), SURGIPRO, TRELEX, ATRIUM and MERSELENE. Absorbable materials, including polyglactin (VICRYL) and polyglycolic acid (DEXON), may be suitable for applications involving temporary repair of tissue or wall defects. It also is contemplated that the mesh fabric may be formed from multifilament yarns and that woven, molded and other suitable methods of forming prosthetic mesh materials may be employed.

In one embodiment, the barrier 24 is formed from a sheet of expanded polytetrafluoroethylene (ePTFE), such as GORETEX available from W. L. Gore & Associates, Inc., having a pore size (submicronal) that discourages tissue ingrowth and adhesion. A representative and non-limiting sampling of other suitable barrier materials includes silicone elastomer, such as SILASTIC Rx Medical Grade Sheeting (Platinum Cured) distributed by Dow Corning Corporation, TEFLON mesh, and microporous polyproplyene sheeting (CELGARD). Autogenous, heterogenous and xenogeneic tissue also are contemplated including, for example, pericardium and small intestine submucosa. Absorbable materials, such as oxidized, regenerated cellulose (Intercede (TC7)) may be employed for some applications. It is to be appreciated that any suitable adhesion resistant materials may be used as would be apparent to one of skill in the art.

In an exemplary embodiment, the composite prosthesis 20 includes an approximately 0.025 to 0.030 inch thick sheet of BARD MESH knitted from polypropylene monofilament with a diameter of approximately 0.006 inches. An approximately 0.003 to 0.005 inch thick sheet of ePTFE is attached to the mesh using approximately 4 mm to 6 mm long stitches formed of a 0.006 inch diameter polypropylene monofilament. The prosthesis 20 has a length along the longitudinal axis of approximately 5.60 inches and a width between the side edges of approximately 2.36 inches. The rounded medial edge 32 has tip radius of approximately 0.47 inches that transitions to a medial side edge radius of approximately 5.95 inches. The barrier 24 has a length along the longitudinal axis of approximately 3.00 inches from the medial edge 32 to the lateral edge 30 thereof with a lateral edge radius of approximately 1.00 inches. These dimensions represent an oversized prosthesis that may be trimmed as necessary by a surgeon to conform to the particular size and shape of the inguinal canal. It should be understood, however, that these dimensions are merely exemplary and that any suitable sizes and shapes may be employed for the prosthesis.

In some instances, it may be desirable to completely isolate the spermatic cord from various potential points of adhesion to the mesh, such as the interior edges of the mesh that are wrapped about the cord to reinforce the internal ring. In one illustrative embodiment shown in FIGS. 4–5, the barrier 24 is provided with a flap 40 extending from the lateral edge 30 of the barrier toward the lateral section 28 of the prosthesis. The flap 40 remains detached from the fabric 22 so that the flap may be lifted away from the fabric and wrapped about the spermatic cord 44, as shown in FIG. 5, as it passes through the fabric.

A keyhole 42 is formed at the end of a slit 46 that extends inwardly from the lateral edge 48 of the fabric to create a pair of tails 50, 52 that are separated to receive the cord 44 in the keyhole. The cord 44 is isolated from the internal edges of the keyhole 42 with the flap 40 as the tails 50, 52 are wrapped about the cord 44 to reinforce the internal ring. The portion of the cord extending toward the medial corner of the inguinal canal is isolated from the fabric 22 by the barrier 24 overlying the medial section 26 of the prosthesis.

One or both of the keyhole 42 and the slit 46 may be preformed with the prosthesis 20 or formed by the surgeon during the repair procedure. Although the slit 46 is shown extending to the keyhole 42 from the lateral edge 48 of the fabric, the slit may extend to the keyhole from any suitable direction, such as transverse to the longitudinal axis from the side edges 34, 36 of the prosthesis.

Figure 4:
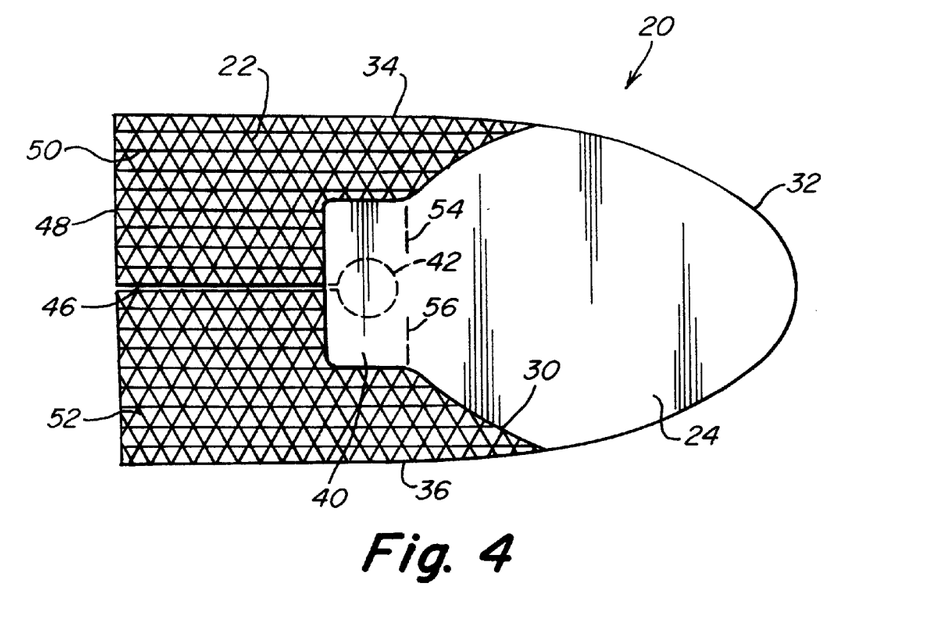
FIG. 4 is a top plan view of a prosthetic repair fabric in accordance with another illustrative embodiment of the present invention.
Figure 5:
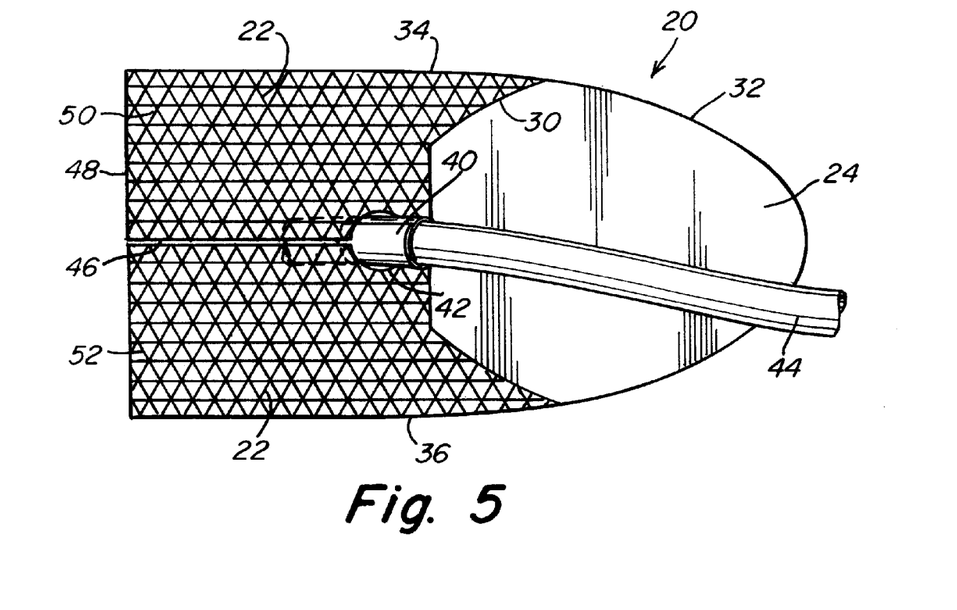
FIG. 5 is a top plan view of the prosthetic repair fabric of FIG. 4 illustrating the spermatic cord being isolated from the internal edges of the fabric with a portion of the barrier being wrapped about the cord as it passes through the prosthesis.

As illustrated in FIG. 4, lateral cuts 54, 56 may be made along the flap 40 by a surgeon to provide a desired flap diameter for wrapping about the cord. In some instances, the flap 40 may be completely removed by the surgeon to allow a limited amount of adhesion between the cord 44 and the edges of the keyhole 42 to create a full ring about the cord.

In one embodiment, the flap 40 has a length of approximately 0.75 inches in a direction along the longitudinal axis and a width of approximately 1.5 inches. It is to be understood that these dimensions are exemplary and that the flap may be configured in any suitable size for isolating the cord as it passes through the mesh.

Figure 6:
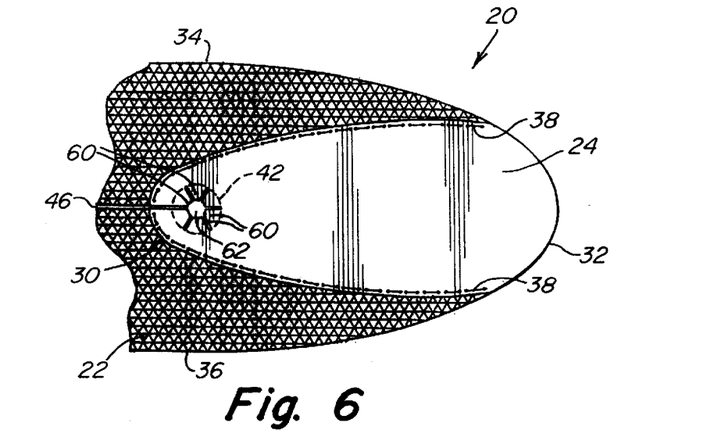
FIGS. 6 and 7 are alternative embodiments for isolating the spermatic cord from the internal edges of the fabric.
Figure 7:
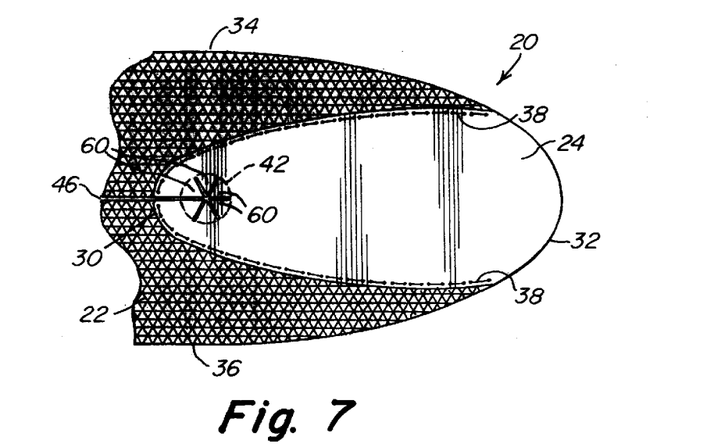

Other illustrative embodiments for isolating the spermatic cord from the internal edges of the mesh are shown in FIGS. 6–7. In FIG. 6, the lateral end of the barrier 24 includes a plurality of flaps 60 surrounding an aperture 62 in the barrier 24 that overlies the keyhole 42 in the underlying fabric 22. The flaps 60 are configured to be collapsed into the keyhole 42 to cover the interior edge of the keyhole and isolate the cord from the fabric edges. In FIG. 7, the barrier 24 includes a plurality of flaps 60 that converge at their tips over the keyhole 42. It is to be understood that any suitable barrier configuration may be implemented to isolate the cord from the mesh as the cord passes through the mesh.

As indicated above, the prosthesis 20 may include a fabric 22 and a barrier 24 having any configuration suitable for providing a desired amount of isolation between the fabric and the spermatic cord in an inguinal hernia repair, while enhancing tissue ingrowth of the host tissue. FIGS. 8–13 illustrate various other embodiments for a prosthesis that may be employed for repairing an inguinal hernia. It is to be appreciated that these embodiments are exemplary and other suitable prosthetic configurations may be implemented for such repairs.

Figure 8:
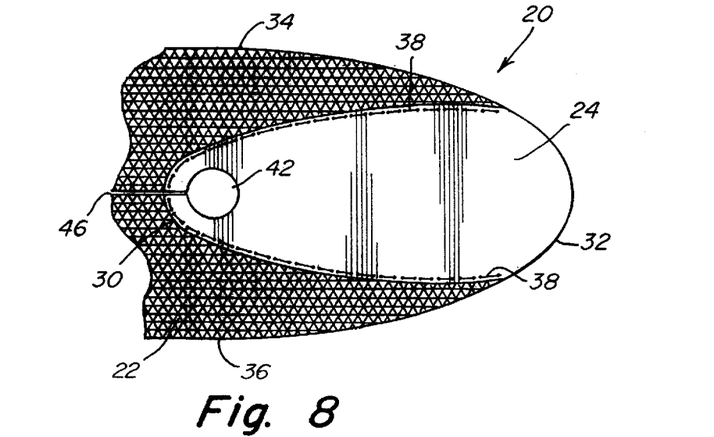
FIGS. 8–13 are fragmentary views of the prosthesis of the present invention illustrating various alternative embodiments.

FIG. 8 illustrates a prosthesis 20 that includes a keyhole 42 through both the barrier 24 and the fabric 22 to receive the cord therethrough. A slit 46 extends from the keyhole 42 to the lateral edge 48 of the prosthesis so that the cord can be routed through the prosthesis.

Figure 9:
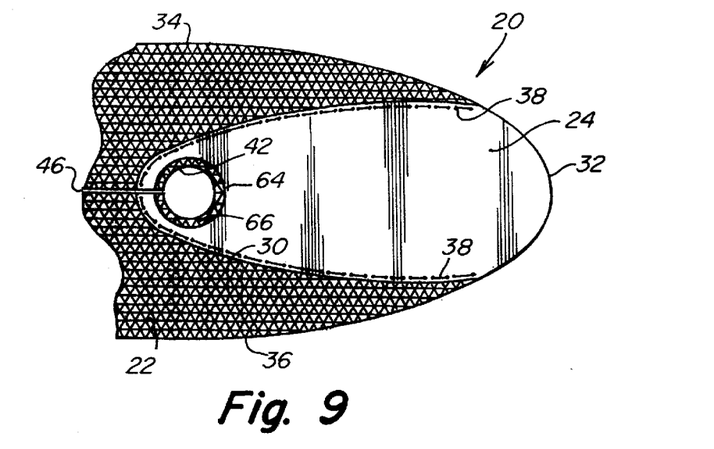

FIG. 9 illustrates a prosthesis 20 that includes a keyhole 42 in the fabric 22 for receiving the cord that is surrounded by an enlarged hole 64 in the barrier 24 that exposes an annular ring 66 of fabric about the cord. This configuration may be implemented when it is desirable to allow a limited amount of cord adhesion as it passes through the prosthesis. A slit 46 extends from the keyhole 42 to the lateral edge 48 of the prosthesis.

Figure 10:
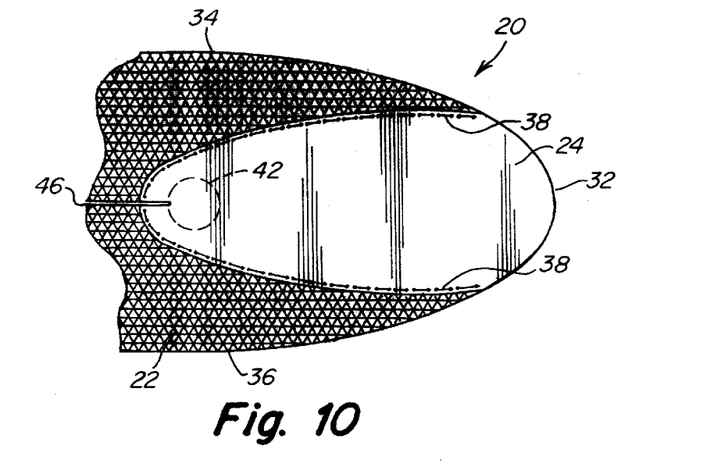

FIG. 10 illustrates a prosthesis 20 having a keyhole 42 in the fabric 22 that is covered by the barrier 24. A slit 46 extends through both the barrier and the fabric from the keyhole 42 to the lateral edge 48 of the prosthesis.

Figure 11:
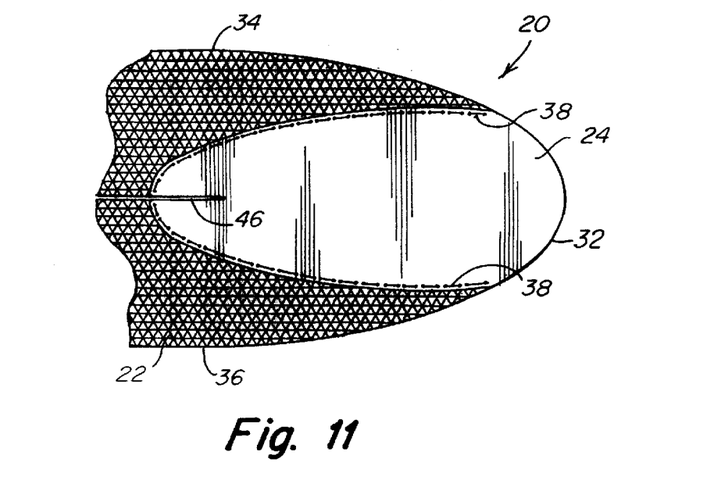

FIG. 11 illustrates a prosthesis 20 that includes a slit 46 extending from the lateral region of the barrier 24 to the lateral edge 48 of the prosthesis. The prosthesis lacks any preformed holes for receiving the cord.

Figure 12:
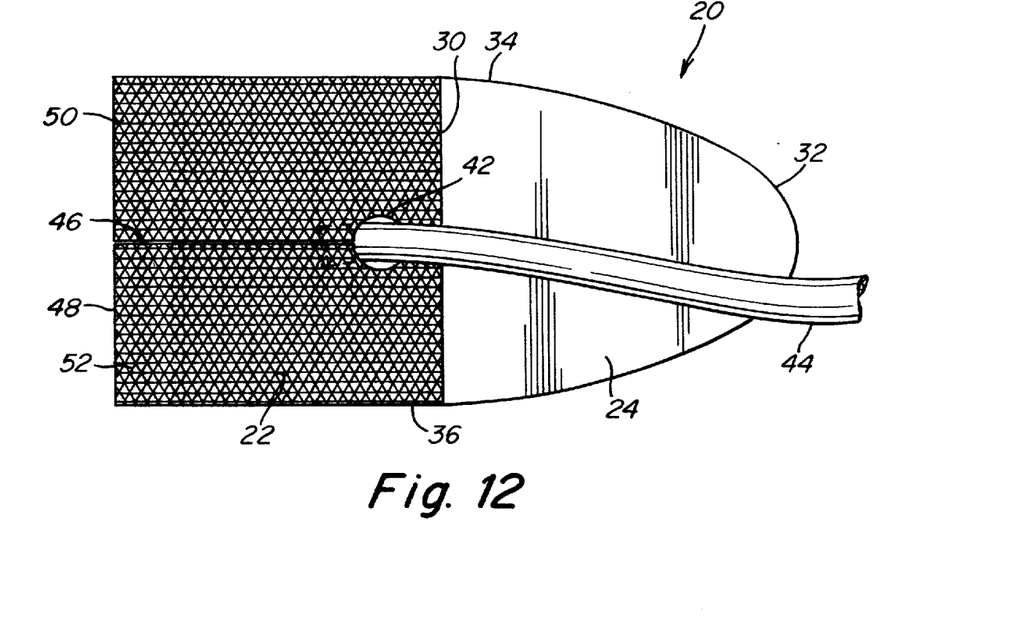

FIG. 12 illustrates a prosthesis 20 that includes a barrier 24 with a generally straight lateral edge 30 positioned toward the medial edge 32 of the prosthesis and away from a keyhole 42 provided in the fabric 22. This configuration encircles the cord 44 with fabric to promote full tissue ingrowth for forming a full ring about the cord.

Figure 13:
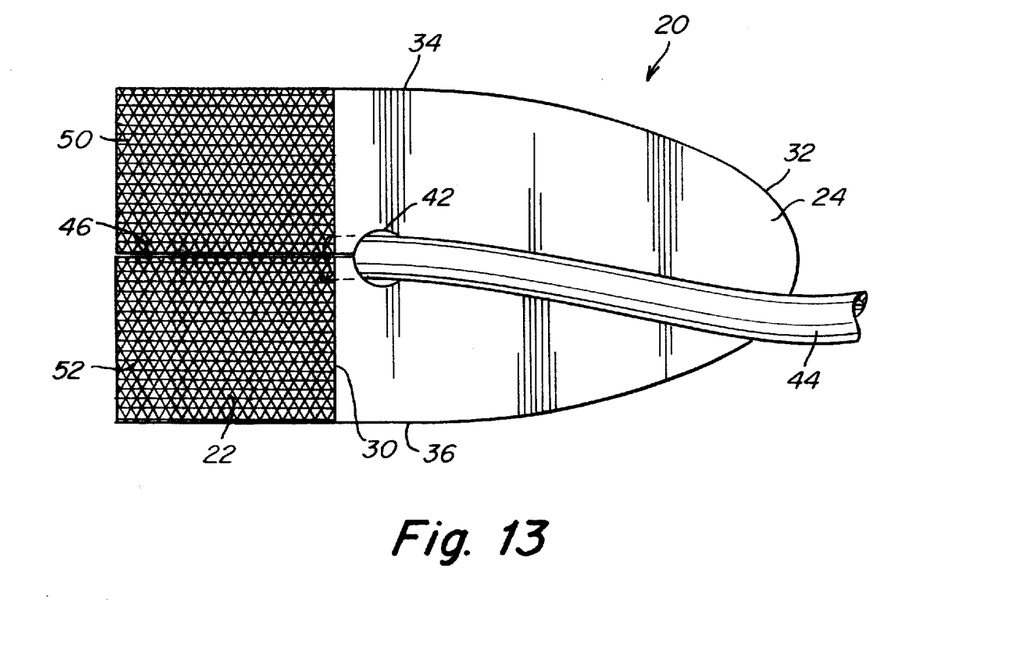

FIG. 13 illustrates a prosthesis 20 that includes a barrier 24 with a generally straight lateral edge 30 positioned on the lateral side of a keyhole 42 in the prosthesis to surround and isolate the cord 44 from the fabric 22.

It is to be appreciated that the various keyhole and slit configurations illustrated FIGS. 8–13 are not intended to be exhaustive. Further, any one or all of the slit and hole configurations may be preformed in the prosthesis or formed by a surgeon during the surgical procedure.

Each of the embodiments illustrated in FIGS. 1–3 and described above includes a symmetrical prosthesis that may be trimmed, as necessary, to conform to the size and shape of the inguinal canal. A symmetrical configuration allows the prosthesis to assume either a left-hand or right-hand configuration to accommodate the off-center position of the spermatic cord within the inguinal canal. It may be desirable in some situations to provide a prosthesis configured specifically for either a left-hand or right-hand inguinal hernia repair to reduce the amount of trimming that may be necessary to conform to the surgical site.

Figure 14:
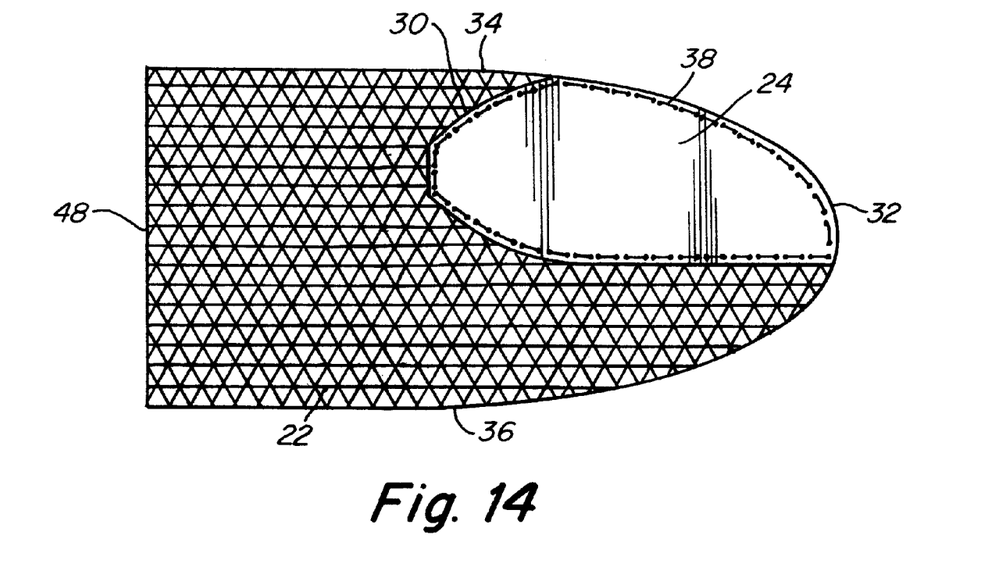
FIGS. 14–17 are top plan views of an asymmetrical prosthesis in accordance with another illustrative embodiment of the invention.
Figure 15:
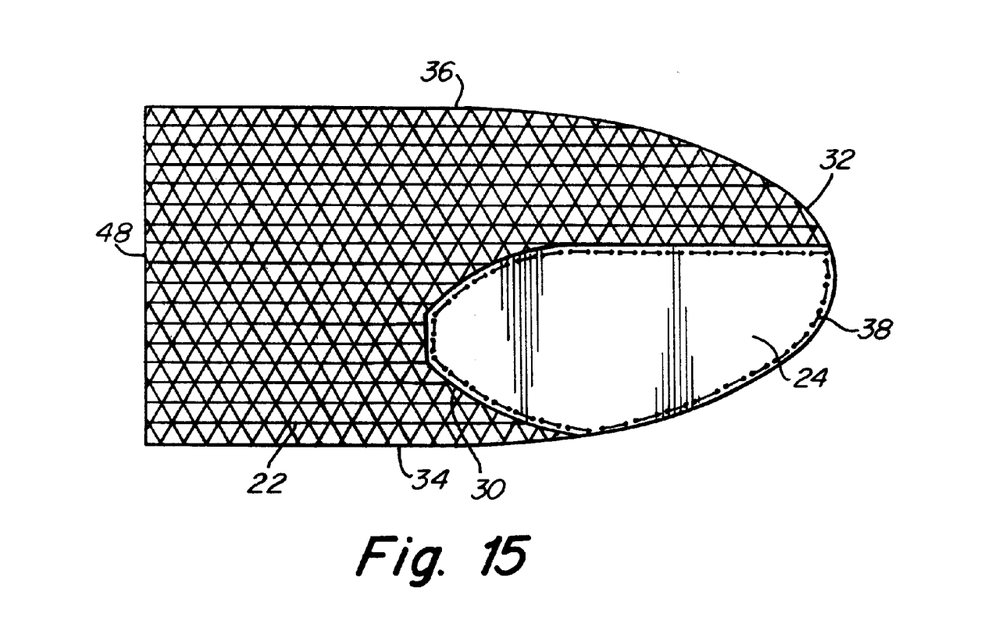

FIGS. 14–15 illustrate one embodiment of a prosthesis formed to have left-hand (FIG. 14) and right-hand (FIG. 15) configurations. As illustrated, the prosthesis 20 has a generally asymmetrical shape with the barrier 24 positioned on the fabric 22 so that the lateral edge 30 of the barrier is shifted more toward one of the side edges 34, 36 of the prosthesis.

Figure 16:
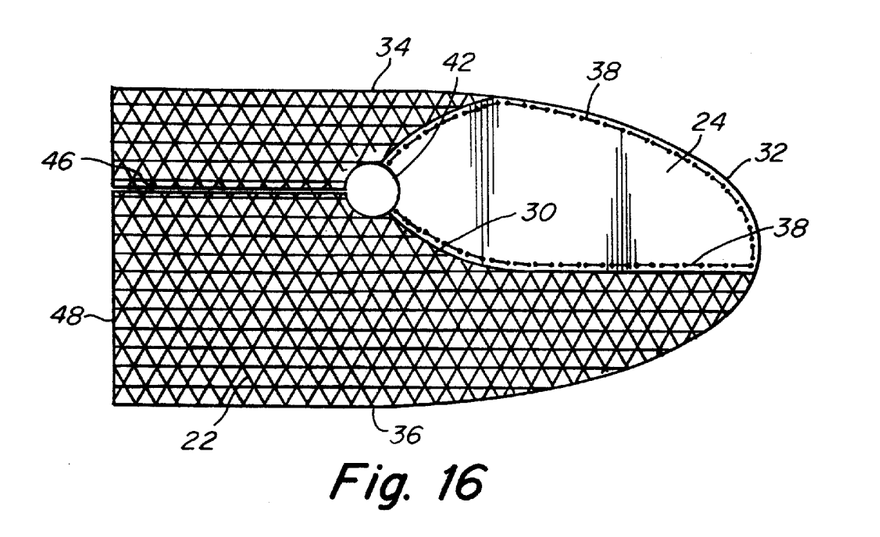
Figure 17:
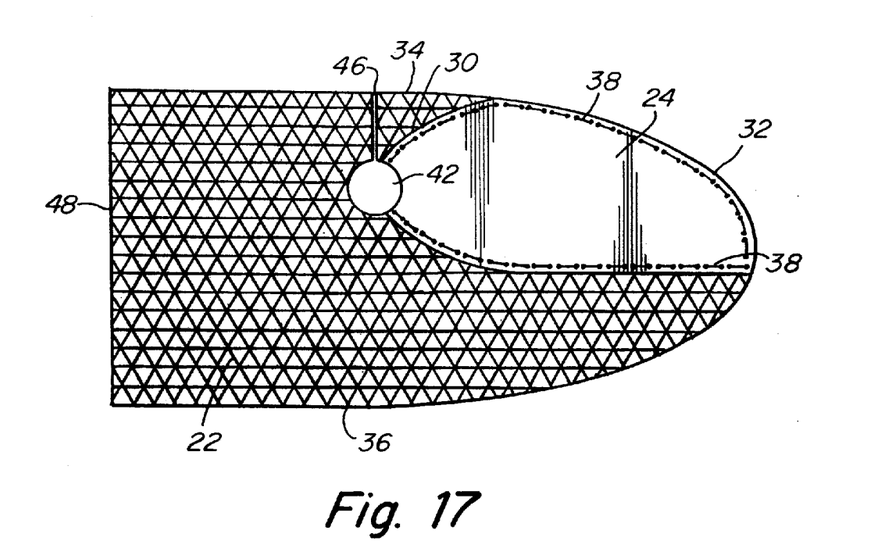

FIGS. 16–17 are illustrative embodiments of a left-hand prosthesis that includes an offset keyhole 42 along the lateral edge 30 of the barrier 24. The keyhole 42 may be partially surrounded along its medial edge with the barrier 24. As shown in FIG. 16, a slit 46 may extend to the keyhole in a longitudinal direction from the lateral edge 48 of the fabric 22. Alternatively, as shown in FIG. 17, a slit 46 may extend to the keyhole 42 in a transverse direction from a side edge 34 of the fabric. A transverse slit may be desirable in some applications to reduce the amount of suturing.

Figure 18:
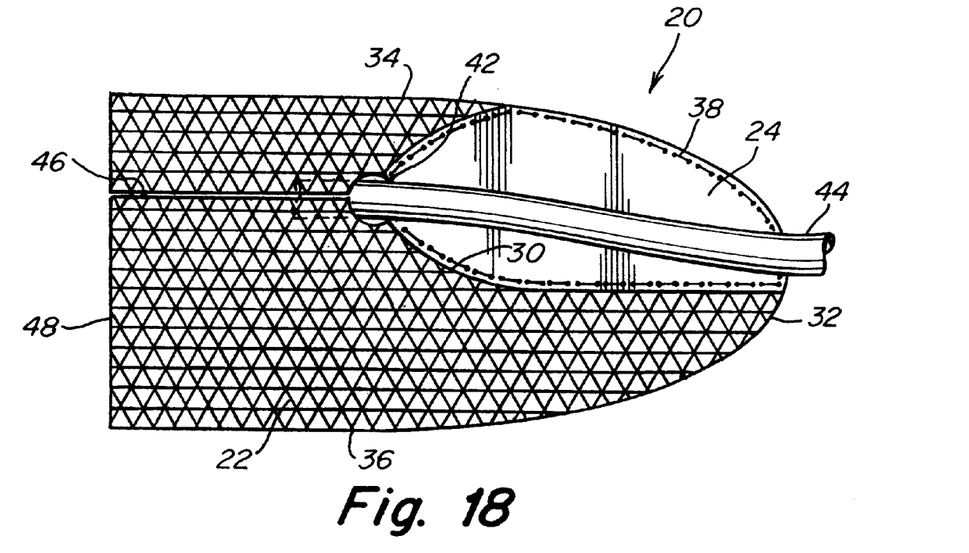
FIGS. 18 and 19 are top and bottom plan views, respectively, of an asymmetrical prosthesis configured for both left-hand and right-hand applications according to a further illustrative embodiment of the invention.
Figure 19:
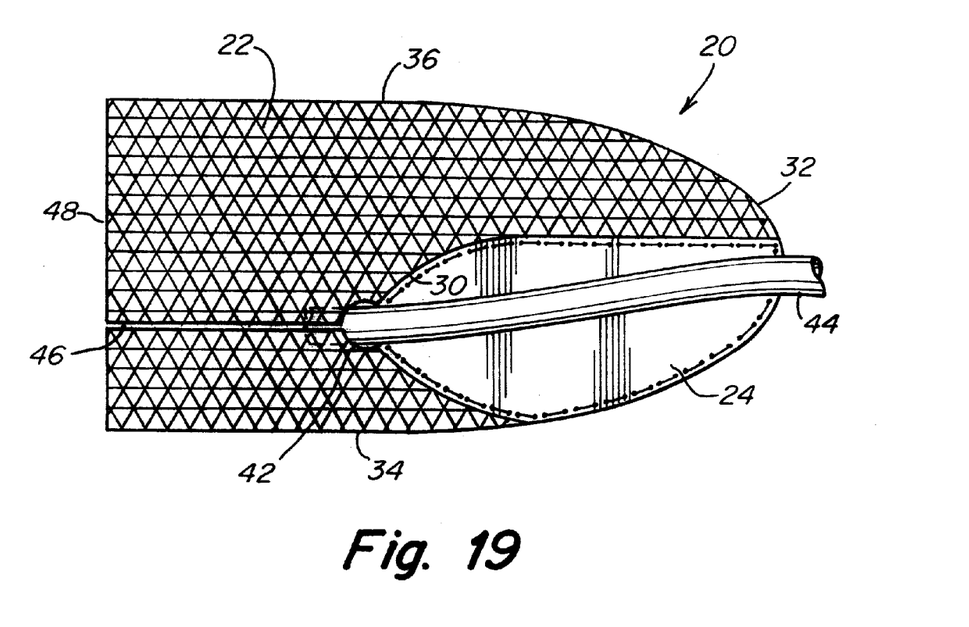

FIGS. 18 and 19 illustrate an alternate embodiment of an asymmetrical prosthesis 20 that is configured for both left-hand (FIG. 18) and right-hand (FIG. 19) applications. The dual role prosthesis includes a pair of barriers 24 that are attached to the top and bottom surfaces of the fabric 22. Similar to the various embodiments described above, a keyhole 42 and slit 46 may be provided with the prosthesis or formed by the surgeon during the repair procedure.

The present invention provides a prosthetic repair fabric having certain of the following advantages. The composite prosthesis combines the low adhesion incidence of a physical barrier with maximum tissue ingrowth to the host tissue. The composite may be anchored in place by tissue ingrowth into the mesh interstices and/or may be sutured, stapled and the like to tissue. The specific pattern of attachment (adhesive, fusion, molding, stitching, etc.) of the mesh fabric and barrier provides a dimensionally strong implant without detrimentally affecting tissue infiltration.

The composite of the present invention is particularly indicated for repair of inguinal hernias for reducing the potential incidence of spermatic cord adhesion, erosion, constriction and the like.

It should be understood that the foregoing description of the invention is intended merely to be illustrative thereof and that other embodiments, modifications, and equivalents of the invention are within the scope of the invention recited in the claims appended hereto.

What is claimed is:

1. A prosthetic repair fabric for repairing a tissue or muscle wall defect located in the inguinal canal near the spermatic cord, the inguinal canal having a medial corner and a lateral end, the prosthetic repair fabric comprising:

a layer of mesh fabric with a plurality of interstices that are constructed and arranged to allow tissue ingrowth, the mesh fabric being susceptible to the formation of adhesions with sensitive tissue and organs, the mesh fabric including a medial section and a lateral section that are configured to be positioned adjacent the medial corner and the lateral end of the inguinal canal, respectively, when the prosthetic repair fabric is placed in the inguinal canal; and at least one barrier layer that inhibits the formation of adhesions with sensitive tissue and organs, the barrier layer being disposed on at least one side of the layer of mesh fabric to cover at least a portion of the medial section that is to be positioned adjacent the spermatic cord when the prosthetic repair fabric is placed in the inguinal canal, the barrier layer to inhibit the formation of adhesions between the spermatic cord and the mesh fabric;

at least a portion of the lateral section of the mesh fabric being free of the barrier layer on both sides thereof to enhance tissue ingrowth therein.

2. The prosthetic repair fabric according to claim 1, wherein the medial section includes a rounded medial edge configured to approximate the shape of the medial corner of the inguinal canal, the barrier layer being configured to conform to the medial edge.

3. The prosthetic repair fabric according to claim 2, wherein the barrier layer includes a rounded lateral edge opposite the medial edge.

4. The prosthetic repair fabric according to claim 3, wherein the barrier layer has a generally tear drop shape.

5. The prosthetic repair fabric according to claim 2, wherein the layer of mesh fabric and the barrier layer are connected by a series of stitches.

6. The prosthetic repair fabric according to claim 5, wherein the series of stitches includes at least one series of continuous stitches having a stitch pattern, at least a portion of the stitch pattern approximating the shape of the medial edge.

7. The prosthetic repair fabric according to claim 6, wherein a central portion of the barrier layer is substantially free of the series of stitches.

8. The prosthetic repair fabric according to claim 6, wherein the at least one series of continuous stitches includes a pair of continuous stitches, the stitch pattern for each of the pair of continuous stitches approximating the shape of the medial edge.

9. The prosthetic repair fabric according to claim 1, wherein each of the layer of mesh fabric and the barrier layer includes a medial edge and a lateral edge opposite the medial edge, the medial edge of the barrier layer being disposed adjacent the medial edge of the layer of mesh fabric and the lateral edge of the barrier layer being disposed intermediate the medial and lateral edges of the layer of mesh fabric.

10. The prosthetic repair fabric according to claim 9, wherein a substantial portion of the lateral section is free of the barrier layer.

11. The prosthetic repair fabric according to claim 10, wherein the lateral edge of the barrier layer is located proximate a central portion of the layer of mesh fabric.

12. The prosthetic repair fabric according to claim 1, wherein the barrier layer includes at least one flap that is separable from the layer of mesh fabric, the flap being foldable through the layer of mesh fabric to isolate the spermatic cord from an internal edge of the layer of mesh fabric when the spermatic cord is routed therethrough.

13. The prosthetic repair fabric according to claim 12, wherein the layer of mesh fabric has an aperture adapted to receive the spermatic cord therethrough, the flap being positioned adjacent the aperture.

14. The prosthetic repair fabric according to claim 13, wherein the at least one flap includes a plurality of flaps disposed about the aperture.

15. The prosthetic repair fabric according to claim 12, wherein the flap includes at least one portion that is constructed and arranged to be wrapped about the spermatic cord.

16. The prosthetic repair fabric according to claim 1, wherein the layer of mesh fabric includes a slit extending inwardly from an outer edge thereof toward the barrier layer.

17. The prosthetic repair fabric according to claim 16, wherein the layer of mesh fabric further includes a keyhole positioned adjacent the barrier layer, the slit extending from the keyhole to the outer edge of the layer of mesh fabric.

18. The prosthetic repair fabric according to claim 16, wherein the slit extends in a longitudinal direction along the lateral section to form a pair of tails that are configured to receive the spermatic cord therebetween.

19. The prosthetic repair fabric according to claim 1, wherein the layer of mesh fabric is formed from polypropylene.

20. The prosthetic repair fabric according to claim 1, wherein the barrier layer is formed from ePTFE.

21. The prosthetic repair fabric according to claim 1, wherein the layer of mesh fabric and the barrier layer are symmetric.

22. The prosthetic repair fabric according to claim 1, wherein the at least one barrier layer is asymmetric.

23. The prosthetic repair fabric according to claim 1, wherein the at least one barrier layer includes a pair of barrier layers disposed on opposite sides of the layer of mesh fabric, the layer of mesh fabric being disposed between the pair of barrier layers.

24. A prosthetic repair fabric for repairing a tissue or muscle wall defect located in the inguinal canal near the spermatic cord, the inguinal canal having a medial corner and a lateral end, the prosthetic repair fabric comprising:

a layer of mesh fabric with a plurality of interstices that are constructed and arranged to allow tissue ingrowth, the mesh fabric being susceptible to the formation of adhesions with sensitive tissue and organs, the mesh fabric including a medial section and a lateral section that are configured to be positioned adjacent the medial corner and the lateral end of the inguinal canal, respectively, when the prosthetic repair fabric is placed in the inguinal canal; and at least one barrier layer that inhibits the formation of adhesions with sensitive tissue and organs, the barrier layer being disposed on at least one side of the layer of mesh fabric to inhibit the formation of adhesions between the spermatic cord and the mesh fabric, the barrier layer including at least one flap constructed and arranged to be folded through the mesh fabric to isolate the spermatic cord from internal edges of the mesh fabric when the spermatic cord is routed through the prosthesis.

25. The prosthetic repair fabric according to claim 24, wherein the layer of mesh fabric has an aperture adapted to receive the spermatic cord therethrough, the flap being positioned adjacent the aperture.

26. The prosthetic repair fabric according to claim 25, wherein the at least one flap includes a plurality of flaps disposed about the aperture.

27. The prosthetic repair fabric according to claim 24, wherein the flap includes at least one portion that is constructed and arranged to be wrapped about the spermatic cord.

28. The prosthetic repair fabric according to claim 24, wherein the layer of mesh fabric includes a slit extending inwardly from an outer edge thereof toward the flap.

29. The prosthetic repair fabric according to claim 28, wherein the layer of mesh fabric further includes a keyhole positioned adjacent the flap, the slit extending from the keyhole to the outer edge of the layer of mesh fabric.

30. The prosthetic repair fabric according to claim 28, wherein the slit extends in a longitudinal direction along the lateral section to form a pair of tails that are configured to receive the spermatic cord therebetween.

31. The prosthetic repair fabric according to claim 24, wherein each of the layer of mesh fabric and the barrier layer includes a medial edge and a lateral edge opposite the medial edge, the medial edge of the barrier layer being disposed adjacent the medial edge of the layer of mesh fabric and the lateral edge of the barrier layer being disposed intermediate the medial and lateral edges of the layer of mesh fabric, the flap being disposed at the lateral edge of the barrier layer.

32. The prosthetic repair fabric according to claim 31, wherein a substantial portion of the lateral section is free of the barrier layer.

33. The prosthetic repair fabric according to claim 32, wherein the flap is located proximate a central portion of the layer of mesh fabric.

34. The prosthetic repair fabric according to claim 31, wherein the medial edges of the layer of mesh fabric and the barrier layer are rounded medial to approximate the shape of the medial corner of the inguinal canal.

35. The prosthetic repair fabric according to claim 34, wherein the layer of mesh fabric and the barrier layer are connected by a series of stitches, the flap being free of the series of stitches.

36. The prosthetic repair fabric according to claim 35, wherein the series of stitches includes at least one series of continuous stitches having a stitch pattern, at least a portion of the stitch pattern approximating the shape of the rounded medial edges.

37. The prosthetic repair fabric according to claim 36, wherein the at least one series of continuous stitches includes a pair of continuous stitches, the stitch pattern for each of the pair of continuous stitches approximating the shape of the rounded medial edges.

38. The prosthetic repair fabric according to claim 24, wherein the layer of mesh fabric is formed from polypropylene.

39. The prosthetic repair fabric according to claim 24, wherein the barrier layer is formed from ePTFE.

40. The prosthetic repair fabric according to claim 24, wherein the layer of mesh fabric and the barrier layer are symmetric.

* * * * *